United States Patent [19]

Luschen et al.

[11] 4,290,426

[45] Sep. 22, 1981

[54] DISPENSER FOR DISPENSING BENEFICIAL AGENT

[75] Inventors: Joseph G. Luschen, Los Gatos; Felix Theeuwes, Los Altos, both of Calif.

[73] Assignee: ALZA Corporation, Palo Alto, Calif.

[21] Appl. No.: 108,515

[22] Filed: Dec. 31, 1979

Related U.S. Application Data

[63] Continuation-in-part of Ser. No. 902,678, May 4, 1978, abandoned.

[51] Int. Cl.³ .............................................. A61M 7/00
[52] U.S. Cl. .................................................. 128/260
[58] Field of Search ........ 128/127, 130, 222, 260–261, 128/270–271; 424/16, 19, 22

[56] References Cited

U.S. PATENT DOCUMENTS

| | | | |
|---|---|---|---|
| 3,630,200 | 12/1971 | Higuchi | 128/260 |
| 3,851,648 | 12/1974 | Brooke | 128/260 |
| 3,975,350 | 8/1976 | Hudgin et al. | 128/260 |
| 4,056,496 | 11/1977 | Mancini et al. | 128/260 |
| 4,064,086 | 12/1977 | Cowsar et al. | 128/260 |
| 4,164,560 | 8/1979 | Folkman et al. | 128/260 |
| 4,203,442 | 5/1980 | Michaels | 128/260 |
| 4,217,898 | 8/1980 | Theeuwes | 128/260 |

*Primary Examiner*—C. Fred Rosenbaum
*Attorney, Agent, or Firm*—Paul L. Sabatine; Edward L. Mandell

[57] ABSTRACT

A dispenser is disclosed for dispensing a beneficial agent to a fluid environment. The dispenser comprises an impermeable container, a reservoir, a passageway, a beneficial agent, and a polymeric agent. In operation, beneficial agent is dispensed by fluid entering the reservoir motivating the polymeric agent to undergo fluid induced transition to a viscofluid, with beneficial agent dispensed by (a) viscofluid exiting through the passageway and transporting beneficial agent concurrently therewith, or by (b) beneficial agent exhibiting an increased coefficient of diffusion in the viscofluid and diffusing therethrough to the exterior of the device. An embodiment of the invention pertaining to laminates also is disclosed as useful for manufacturing the dispenser.

25 Claims, 11 Drawing Figures

DISPENSER FOR DISPENSING BENEFICIAL AGENT

CROSS REFERENCE TO RELATED APPLICATION

This application is a continuation-in-part of United States Patent Application Ser. No. 902,678 filed on May 4, 1978, and now abandoned which application is incorporated herein by reference and benefit is claimed of its filing date. These applications are assigned to the ALZA Corporation of Palo Alto, Calif.

FIELD OF THE INVENTION

This invention pertains to both a novel and useful dispenser. More particularly, the invention relates to a dispenser that dispenses a beneficial agent to a fluid environment of use at a rate governed by fluid induced relaxation of a polymeric agent over a prolonged period of time.

BACKGROUND OF THE INVENTION

In recent times, efforts have been advanced for manufacturing devices that dispense a beneficial agent to an environment in need of same. Generally, these devices possess useful fabrication and dispensing characteristics; however, the devices frequently have serious disadvantages associated with their structure and their use. For example, U.S. Pat. No. 3,146,169 issued to Stephenson, et al. discloses a device consisting of a solid inner medication portion readily dissolvable in fluids and an outer portion insoluble in fluids that surrounds the dissolvable inner portion. An aperture extends through the outer portion to the inner medicated portion. The inner portion is released by dissolving it in fluid that enters through the aperture to the exterior of the device. In this device, medication thus is released by uncontrolled dissolution predicated upon many variables. The variables include the rate of medication dissolution which is pH dependent and varies according to the environment; and when the pH changes, it increases or decreases the solubility of the medication and its rate of release is changed correspondingly. The rate of release from the device also is stirring rate dependent. An external fluid must be in continual contact with the medication to cause dissolution of the inner portion for its release from the device. Hence, if the motion of fluid external to the device is changed, the diffusion path length changes, and a turbulence is created, altering the rate of release from the device. In this device, the exposed surface area of the inner portion also is continually changing at an uncontrolled rate, which results in release of the inner portion in varying amounts. This feature seriously limits the usefulness of the device. Moreover, as the exposed surface area of the inner portion and the length of the diffusional path changes, the amount of inner portion released becomes unpredictable, and as such, this device cannot be relied upon for effective use in the management of health and disease.

In U.S. Pat. Nos. 3,851,648 and 3,924,622 issued to patentee Brooke, a device is disclosed for releasing a diffusible solid. The device consists essentially of a container, a slot in the container, and an inner cavity in the container. The cavity is defined by an accurate wall, and has a pie shaped and it is always changing to a larger pie-shaped cavity. In the patents issued to Brooke, as the path length of the drug travels to exit the device increases, so does the releasing surface of drug, and the ever growing pie-shaped cavity. The releasing surface of drug must grow and increase to compensate for the increased drug path to obtain zero-order release. The device also has a pair of parallel congruent planar end walls at right angles to the slot, and a pair of inwardly extending congruent planar side walls adjacent to the opposite sides of the slot, in divergent radial relation to the slot and extended to the rear wall. A means is present in the cavity in bonded relation to the inner wall for diffusion solid from within the cavity. This device also has certain critical disadvantages that tend to restrict its use. For example, the device appears hard to manufacture. The device is hard to make because the device has an intricate geometric configuration that places severe demands upon the procedure. Also, the device seemingly does not lend itself to exact controlled delivery because the internal structure of the device has a shape that is cumbersome to make, particularly since it has angles and surfaces that require high precision in manufacture, as these embodiments must keep their selected relationship during use. The desired results are hard to obtain because the device requires an increasing surface area of diffusible solid exposed to fluid, as the length of the path through which the dissolved solid must diffuse to reach the exterior of the device. The parameters embraced by the device limits its appeal. Thus, in view of the deisgn and manufacture problems associated with the prior art, it will be appreciated by those versed in the art that if a device is provided that is free from the tribulations generally associated with the prior art, such a device would be a useful article of manufacture and represent an advancement in the dispensing arts.

OBJECTS OF THE INVENTION

Accordingly, it is an immediate object of this invention to provide a new and useful dispensing device that overcomes the aforesaid disadvantages associated with the prior art.

Yet still another object of the invention is to provide a device for releasing a drug using a polymeric agent that undergoes transition from one physical state to another state during use for the controlled release of drug over a prolonged period of time.

Yet still another object of the invention is to provide a dispensing device that is easy to manufacture, can be used economically, and can dispense a beneficial agent at a dependable rate to a biological environment over time.

Still yet another object of the invention is to provide a dispensing device that has means in the device that occupies a volume having a substantially constant cross-sectional area parallel to the passageway of the device that release agent therefrom at a substantially zero-order rate over time.

Still yet another object of the invention is to provide a dispensing device having an oscillating rate of release pattern, which rate changes periodically from a maximum to a minimum rate of release over time.

Still yet another object of the invention is to provide a device having an increasing rate of release followed by a constant rate of release over time.

Yet still another object of this invention is to provide a reliable and easy to use dispenser for administering controlled amounts of beneficial agent to an agent receptor site with the dispenser keeping its physical and chemical integrity during use.

Still another object of the invention is to provide a dispenser that administers a complete dosage regimen for a particular time period, the use of which requires intervention only for initiation of the regimen.

Other objects, features and advantages of the invention will be apparent to those skilled in the art from the detailed description of the invention which follows, taken in conjunction with the drawings and the accompanying claims.

SUMMARY OF THE INVENTION

The invention concerns a device for dispensing a beneficial agent. The device comprises an impermeable container, having a reservoir and passageway. The reservoir houses a polymer and a beneficial agent. Beneficial agent is dispensed by the polymer imbibing fluid, by which process the polymer undergoes relaxation, thereby releasing agent from the device. The relaxation occurs at the boundary distinguishing the polymer containing imbibed fluid from the polymer essentially free of imbibed fluid. Beneficial agent is dispensed by the relaxed polymer being dispensed from the device transporting agent therewith, or by agent dissolving in relaxed polymer and diffusing to the exterior of the device. The amount of beneficial agent dispensed is governed by the rate of relaxation of the polymer over time.

BRIEF DESCRIPTION OF THE INVENTION

In the drawings, which are not drawn to scale, but are set forth to illustrate various embodiments of the invention, the Figures are as follows.

In the drawings and specifications, like parts in related figures are identified by like numbers. The terms appearing earlier in the specification and in the description of the drawings, as well as embodiments thereof are further described elsewhere in this application.

DETAILED DESCRIPTION OF THE DRAWINGS

Figure 1:
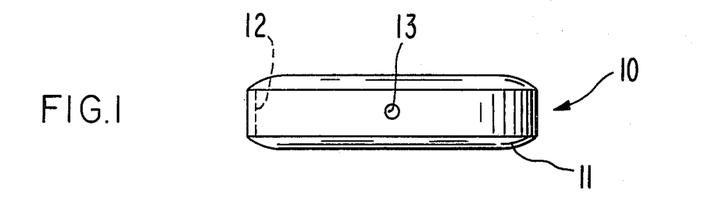
FIG. 1 is a side view of device of this invention made with a single orifice and designed for delivering an active agent.

Turning now to the drawings in detail, which are examples of devices of the invention, and which examples are not to be construed as limiting, one embodiment manufactured as a device is seen in FIG. 1 indicated by the numeral 10. Device 10 comprises a body 11 formed of a wall 12 that surrounds and forms a reservoir, not shown in FIG. 1, which reservoir communicates through orifice 13 with the exterior of device 10.

Figure 2:
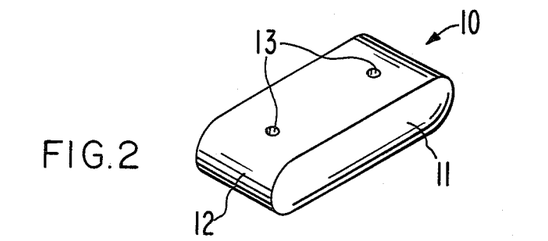
FIG. 2 is a view of a device of the invention similar to the device of FIG. 1 and made with two orifices for delivering an active agent.

FIG. 2 is similar to FIG. 1. FIG. 2 illustrates device 10 comprising body 11 formed with wall 12 that surrounds and forms and internal reservoir, not seen in FIG. 2. Wall 12 is made of a material that is substantially impermeable to the passage of fluid and substantially impermeable to the passage of compounds and solutes. Device 10 is made with two orifices 13 that extend through wall 12 thereby communicating the exterior of device 10 with the internal reservoir. Orifices 13 in device 10 are spaced apart and they can be used for like or unlike purposes. That is, orifices 13 can be oriented to deliver agent to different receptor sites. Orifices 13 can have the same or different areas for both aiding in regulating the amount of fluid that enters device 10, or in governing the amount of beneficial agent delivered from device 10 per unit time over a prolonged period of time.

Figure 3:
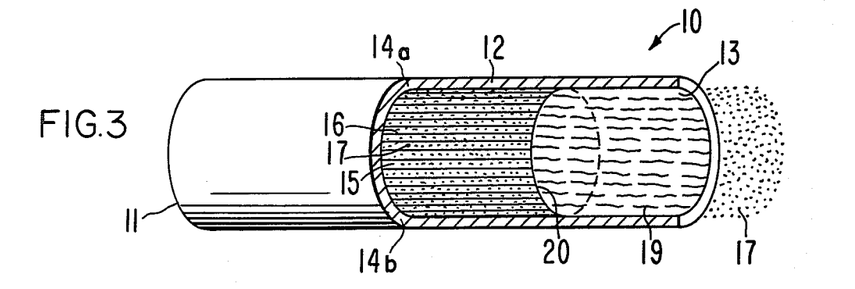
FIG. 3 depicts a device of the invention made with a single orifice and seen in opened section for illustrating the internal operation of the device.

FIG. 3 illustrates device 10 drawn for viewing the structure thereof operating as an integral unit device. Device 10, as seen in FIG. 3, consists of body 11 formed of wall 12. Wall 12 has a part removed to form an opened section at 14a to 14b for depicting the internal structure of device 10. Wall 12 surrounds and forms a reservoir 15 that communicates with the exterior of device 10 through orifice 13. Wall 12 is formed of materials that is essentially imperforate, impermeable to fluid and impermeable to agents and solutes. Wall 12 is formed of a synthetic or naturally occurring material, that is non-toxic in biological environment, and maintains its physical and chemical integrity during the prolonged period of time beneficial agent is delivered from the device. A detailed description of materials suitable for forming wall 12 appears later in the specification.

Wall 12 surrounds and forms reservoir 15, an internal compartment. Reservoir 15 houses polymeric agent 16, depicted by parallel lines, which polymeric agent 16 contains beneficial agent 17 mixed therein, and depicted by dots. Polymeric agents 16 suitable for the purpose of the present invention, generally include polymeric agents that can be initially present in reservoir 15 in an unrelaxed physical state, and undergo transition when device 10 is in operation in the environment of use to relaxed physical state 19, depicted by wavy lines. Polymeric agent 16 undergoes relaxation as fluid enters device 10 through orifice 13 and is osmotically imbibed by polymeric agent 16. As fluid sorption takes place, relaxation occurs at moving boundary 20 between substantially fluid saturated relaxed polymeric agent 16 now in a viscofluid mechanical state, and fluid unpenetrated polymeric agent 16. Boundary 20 illustrates the releasing surface of polymeric agent 16, which latter agent is a means occupying a volume having a constant cross-sectional area parallel to the passageway 13 for releasing beneficial agent 17 at a substantially zero order rate. The distance agent 17 travels before leaving system 10 decreases in the illustrated embodiment. This is attributable to the shape of the device acting in cooperation with the fluid uptake and the resultant transition of the polymeric means 16 expanding towards passageway 16. That is, polymeric agent 16, in both the relaxed and the unrelaxed states occupies a volume that has a cross-sectional area parallel to orifice 13 during the period time beneficial agent 17 is dispensed from device 10.

In operation, device 10 dispenses beneficial agent 17 by two physical chemical operations. In one operation, polymeric agent 16 absorbs fluid that enters reservoir 15 and undergoes fluid induced relaxation from an initial unrelaxed 16 to relaxed state 19. In this latter state, beneficial agent 17 exhibits an increased coefficient of diffusion with beneficial agent 17 dispensed to the exterior of device 10 by passing by the process of diffusion through relaxed polymer 19. The amount of beneficial agent 16 dispensed from device 10 occurs at a relaxed controlled delivery rate. This rate is dependent on the amount of beneficial agent 17 present in relaxed polymeric state 19, with relaxation occurring at a rate governed by the progressive fluid imbibition by unrelaxed polymeric agent 16, and the accompanying fluid induced rate of relaxation over time. In another operation, relaxed polymeric agent 19 functions as a means for transporting beneficial agent 16 mixed therein from device 10. In this operation, as polymeric agent 16 imbibes fluid and undergoes fluid induced relaxation, which relaxation is often accompanied by swelling and formation of a rubbery phase, it, 19, functions as a transporting agent in relaxed state 19, and as it, 19, flows through passageway 13 to the exterior of device 10, it transports beneficial agent 17 concurrently therewith. The rate of beneficial agent released from device 10 is relaxation controlled, as the fluid penetrant is continually imbibed and the boundary progressively moves parallel to passageway 13 along the polymeric front and urges formation of the relaxed transporting state 19.

Figures 4, 5:
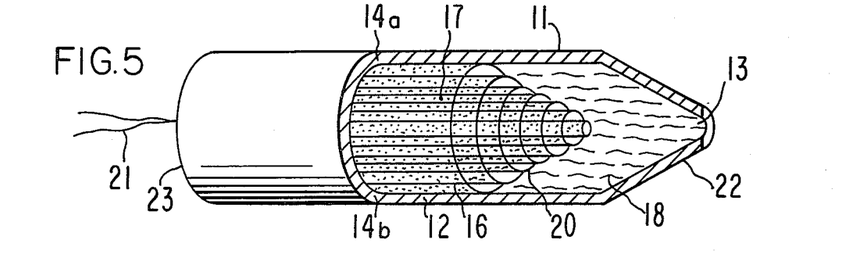
FIG. 4 represents a diagrammatic view of a device of the invention made with two orifices illustrating the device delivering beneficial agent through both orifices.
FIG. 5 is another embodiment of the invention showing a device with a different release pattern and having a section of its impermeable wall removed for viewing the structure of the device, with the device designed for delivering an agent in a body canal.

FIG. 4 illustrates a device 10 similar to the devices seen in FIGS. 2 and 3, and it is manufactured with identical components that operate as a fully integrated, unit dispensing device. Device 10 of FIG. 3 is made with two orifices 13. Each orifice can simultaneously admit fluid and dispense beneficial agent. Device 10 has two boundaries 20 that exist between the relaxed 16 and relaxed 19 states. Dispensing of beneficial agent 17 occurs when soprtion is controlled by fluid induced relaxation occurring at the boundaries between the relaxed, fluid swollen state 18 and the fluid unpenetrated glassy state 16. During steady-state fluid soprtion by device 10, the boundaries move at a constant velocity towards each other, with the device dispensing beneficial agent 17 by operating in the manner described above.

FIG. 5 illustrates another device 10 designed for administering a beneficial agent 17 within a body opening, the anal and vaginal canals, not shown. Device 10 is shaped like an obelisk having a lead end 22, a rear end 23, and it is comprised of body 11, wall 12, with a section removed at 14a and 14b, which wall 12 surrounds reservoir 15 containing polymeric agent 16 with beneficial agent 17 dispensed therein. Beneficial agent 17 can be homogeneously or heterogeneously dispersed therein, and it can be present in dissolved and undissolved forms. Device 10 has a string 21 fixed to rear 23 for pulling device 10 from a biological environment of use. Beneficial agent 17 is released by relaxation mechanisms. That is, as fluid penetrant enters device 10 and polymeric agent 16, fluid plasticization and swelling occurs leading to polymeric relaxation 20 and an increased coefficient of diffusion for the beneficial agent 17 in the polymeric agent 16. The fluid sorption and osmotic swelling is controlled by fluid induced relaxation taking place at a sharp boundary separation the relaxed swollen and unrelaxed, unswollen regions of polymeric agent 16. The obelisk shape of device 10 leads to an increasing rate of release that is followed by a substantially constant rate of release over time. The boundaries 20, progressively moves through 16 at a controlled rate dispensing beneficial agent by the two mechanisms described above. Wall 12 has the properties described above.

Figure 6:
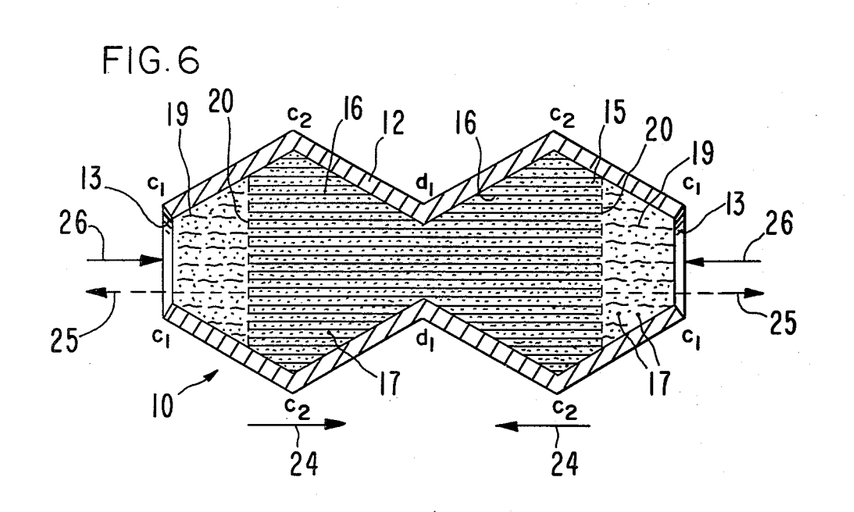
FIG. 6 represents another device made according to the invention. The device of FIG. 6 is designed for an oscillating delivery of drug. The amount of drug dispensed by this device increases then decreases over time as seen in FIG. 6a; and, FIGS. 7, 8, 9 and 10 are graphs that depict the rate of release and other described parameters for devices made according to the spirit of the invention.

FIG. 6 illustrates another device 10 designed for dispensing beneficial agent 17 to an environment of use. In FIG. 6, the structure of device 10 operates in cooperation with the geometric shape of device 10, as a unit device, for programming the release rate profile of beneficial agent 17 from device 10. The environment of use, in a presently preferred embodiment, is a biological environment. Device 10 of FIG. 6 is used for dispensing beneficial agent 16 at a continuous, oscillating rate over time. That is, as external fluid, usually water, enters reservoir 16 of device 10, the amount of beneficial agent 16 dispensed increases from $C_1$ to $C_2$ and then decreases from $C_2$ to $d_1$. The change in the amount of beneficial agent 17 dispensed occurs as the travelling fluid front and its accompanying progressively changing boundaries travel through reservoir 15 of device 10. The device of FIG. 6 is an oscillating release pattern, changing periodically from a maximum to a minimum rate of release over time.

Figure 6A:
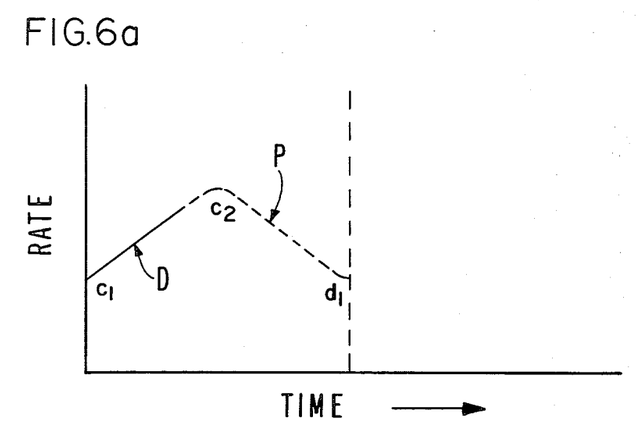

FIG. 6a further depicts the changing rate of release per unit time from device 10 of FIG. 6. In FIG. 6a, the section of the solid curved line labeled D indicates the delivery rate of release of beneficial agent 17, and the curved portion labeled P indicates the programmed rate of release of device 10. Optionally, if one of orifice 13 is absent and replaced by an impermeable wall 12, then the release rate pattern seen in FIG. 6a repeats, and it is approximately one-half the rate of a two-orifice device throughout the history of the device.

FIGS. 6 and 6a, solid arrow 26 pointing into device 10 at orifice 13 indicates the direction of fluid movement into device 10, dashed arrow 25 at 13 indicates the direction of drug movement from device 10, dashed line 20 indicates the boundary of the relaxed-unrelaxed front solid lines 16 indicate unrelaxed polymer, wavy lines 19 indicate relaxed polymer, and solid arrow 24 indicates the direction of movement of the traveling fluid front at the point where polymeric agent 17 undergoes transition to relaxed physical state 19. FIG. 6 operates in a manner similar to FIG. 4, with FIG. 6 additionally having an oscillating drug program manufactured into device 10.

While FIGS. 1 through 6 are illustrative of various devices 10 that can be made according to the invention, it is understood these devices are not to be construed as limiting the invention, as the devices provided by the invention can take a wide variety of shapes, sizes, structures, and forms adapted for delivering beneficial agent to different environments of use. For example, the devices include ear, eye, nose, buccal, oral, vaginal, implant, pessary, prosthetic, cervical, intrauterine, artificial gland, and other devices sized, shaped and adapted for easy placement and prolonged retention in the environment of use. The devices can endorse many shapes. For example, intrauterine devices can by cylindrical, bullet, elliptical, circular, bulbous, loop, bow, or any other shape. Devices for the eye include any geometric shapes for comfortable insertion and prolonged rentention in the cul-de-sac. Typical shapes include ellipsoid, bean, banana, circular, rectangular, doughnut, and half-ring shaped devices. In cross-section, the ocular devices can be double convex, concavo-convex, rectangular and the like, as the device in use will tend to conform to the sape of the eye. The dimensions of the devices can vary with the lower limits governed by the amount of beneficial agent to be supplied to the environment as well as the smallest device that can be placed in the environment of use. The upper limits on the size of the device is governed by the space limitations of the environment consistent with the amount of beneficial agent to be supplied over time.

The devices made for oral use can have various conventional shapes and sizes such as round with a diameter of 3/16 inch to ½ inch, or it can be shaped like a capsule having a range of sizes from triple zero to zero, and from 1 to 8. The devices also can be adapted for delivering beneficial agent in streams, aquariums, fields, factories, reservoirs, laboratory facilities, hot houses, transportation means, naval means, hospitals, veterinary clinics, nursing homes, an other environments of use.

DETAILED DESCRIPTION OF THE INVENTION

In accordance with the practice of the invention, it has now been unexpectedly found the devices of this invention provide many advantages for their use in a wide variety of environments. One advantage is the ease of construction of the devices by standard manufacturing techniques into devices of various shapes, sizes and forms for delivering beneficial agents to the environment of use. Another advantage for the devices is they can be made with a minimum number of parts, in a reproducible manner, and at lower costs. Another advantage for the devices is that release of agent is controlled by the device and not the environment of use. Another advantage of the device is they can be used for dispensing drugs that are soluble and insoluble in aqueous and biological fluids in small to large amounts to the environment of use. Other advantages will become more apparent to those versed in the art from the specification, the drawings and accompanying claims.

The materials suitable for forming wall 12 are generally those materials that are non-toxic, maintain their physical and chemical integrity during the prolonged period of time beneficial agent is dispensed, are essentially impermeable to the passage of aqueous and biological fluids, and essentially impermeable to the passage of beneficial agents, polymers, solutes and ingredients in the device and in the environment of use. Typical material for the present purpose are polymers such as acrylonitrile-styrene copolymer, acrylonitrile-butadiene-styrene terpolymer, poly(monochlorotrifluoroethylene), poly (tetrafluoroethylene), poly(propylene), poly(ethylene), tetrafluoroethylene-hexafluoroethylene copolymers, poly(styrene), butadiene-styrene copolymer, chlorosulfonated polyethylene-styrene copolymer, vinyl chloride-acrylonitrile copolymer, vinylidene chloride-alkylacrylate copolymer, poly(cyclohexane dimethanol-terphthalate), poly(carbonate), and other non-erodible polymers. The impermeable wall forming polymers, in another embodiment of the invention, can be laminated to a lamina of a different wall forming material used for ease of manufacture and for providing physical and mechanical support for the final wall of device 10. Wall 12 of device 10 in all embodiments will always consist essentially of one wall forming material that is both impermeable to the passage of fluids and the agents and ingredients set forth above. Generally, for the present purpose, the wall forming lamina used for supplying physical and mechanical support will be a member selected from the group consisting essentially of semipermeable wall forming cellulose acylate, cellulose diacylate, cellulose triacylate, cellulose acetate, cellulose diacetate, and cellulose triacetate. Wall 12 generally is about 1 mm to 15 mm thick, and when laminated to a different wall forming material each lamina are about 1 to 10 mm thick, for a laminated wall of 1 to 20 mm thick. The polymers are known to the art in U.S. Pat. Nos. 3,290,198; 3,419,421; 3,459,582; and 4,034,758, in *Handbook of Common Polymers*, by Scott and Roff, 1971, published by CRC Press, Cleveland, Ohio, and in *Handbook of Plastics and Elastomers*, by Harper, 1975, published by McGraw-Hill Company, New York.

The expression polymeric agent, 16, as used for the present purpose generically denotes polymeric agents that can undergo change from an energy state characterized as amorphous or crystalline, and undergo transition to an lower energy state characterized a rubbery or viscofluid states. These transitions also can be characterized by the glass-transition and fluid induced relaxation, as seen by the polymeric agent undergoing relaxation from an unrelaxed to a relaxed state. The phrase glass-transition as used herein broadly denotes the fluid induced change of an amorphous polymer from an unrelaxed glassy to a relaxed flexible, rubbery or viscofluid state. The fluid that induces change includes biological fluid and water. Typical polymeric agent 16 that can be used for the purpose of the invention include poly(hydroxyalkyl methacrylates), poly(acrylamide), poly(methacrylamide), poly(N-vinyl-2-pyrrolidone), pharmaceutically acceptable dextrans, anionic and cationic hydrogels, poly(electrolyte) complexes, poly(vinylalcohol), poly(glyceryl methacrylate), poly(hydroxypropyl methacrylate), poly(sulphide), poly(sulphoxide), poly(sulphone), poly(styrene), copolymer of divinylbenzenestyrene, poly(dialkylaminoethyl styrene), strong-acid cation-exchange resins, strong-base anion-exchange resins, sulfonated copolymer of styrene and divinylbenzene, copolymers of methacrylic acid and divinylbenzene, weak-base anion-exchange resins, poly(alkylene oxide), and the like. These polymeric agents are known in Netherlands Pat. No. 7,006,124; West Germany Pat. Nos. DT 1,965,133 and 2,018,690; Great Britain Pat. No. 1,208,693; *Encyclopedia of Polymer Science and Technology*, Volume 7, pages 692, to 742, 1967, published by John Wiley & Sons, Inc., and *J. Chem. Soc.*, pages 2195 to 2919, 1950.

The expression beneficial agent 17 as used herein broadly includes active agents and any compound, formulation, or composition of matter that can be delivered from device 10 to produce a beneficial and useful results. The beneficial agent can be soluble in fluid that enters reservoir 15, or it can exhibit increased solubility in the relaxed polymeric state 19. The beneficial agents include algicides, animal nutrients, anti-oxidants, air purifiers, biocides, catalysts, chemical reactants, cosmetics, canine nutrients, drugs, disinfectants, fungicides, fermentation agents, foods, food supplements, pheromones, fertility inhibitors, fertility promoters, germicides, herbicides, insecticides, micro-organism attenuators, pesticides, plant growth promoters, plant growth inhibitors, preseratives, rodenticides, sex sterilants, sterilization agents, vitamins and viricides, and other agents that benefit the environment of use.

In the specification and the accompanying claims, the term "drugs" includes any physiologically and pharmacologically active substance that produces a localized or systemic effect in animals, avians, reptiles and fishes.

The terms animals as used herein includes mammals, humans, primates, domestic household, sport and farm animals, such a dogs, sheep, goats, cattle, horses and pigs, for administering to laboratory animals such as mice, rats, and guinea pigs, and zoo and jungle animals. The active drug includes inorganic and organic compounds, and drug formulations, such as those materials that act on the central nervous system, the automatic nervous system, hypnotics, sedatives, psychic energizers, tranquilizers, anticonvulsants, muscle relaxants, antiparkinson, analgesics, antipyretics, anti-inflammatory, anethetics, antispasmodics, muscle contractants, antimicrobials, anti-malarials, hormonal agents, progestational, estrongics, androgenic, corticoid, sympathomimetic, cardiovascular, diuretics, antiparasites, neoplastics, hypoglycermics, nutritional, vitamins, amino acids, fats, eye, drugs electrolytes, and the like. The beneficial drugs are known to the art in *Pharmaceutical Sciences*, by Remington, 14th Edition, 1970, published by Mack Publishing Company, Easton, Pa. and in *The Pharmacological Basis of Therapeutics*, by Goodman and Gilman, 4th Edition, 1970, published by the MacMillian Company, London.

The drugs can also be in various forms, such as uncharged molecules, molecular complexes, pharmacologically acceptable esters, ethers and amides. The drug can be in a form that on its release from the device is converted to the original form, or to a biologically active form. The drug can be in the reservoir in the form of particles, granules, powders, and the like. The drug can be mixed with a binder, dispersant, emulsifier, or wetting agent in a drug formulation. Generally, the amount of active agent or drug in the reservoir will be from 0.01 ng to 10 g or more, with individual devices housing 1 mg, 5 mg, 1.6 g, and the like.

The expression pasageway as used herein comprises aperture, orifice, bore, and the like that extends through the wall and connects the reservoir with the exterior of the device. The passageway will have an area that permits the controlled release of agent form the reservoir, and it can be made by mechanical drilling, laser drilling, pelletizing, and the like. In another embodiment, the passageway can be made by coextruding wall 12 and reservoir 15, and then pelletizing or segmenting the extruded embodiment to the manufactured devices.

The devices of the invention are manufactured by standard techniques. For example, one suitable method consists of first making a reservoir forming formulation comprising beneficial agent 17 and polymeric agent 16 by blending the two agents in crystalline, granular or like form, and then applying pressure with or without heat to convert the blended agents into a solid, shaped reservoir forming formulation. The reservoir is sized, shaped and adapted according to the dimensions of the device. Next, the reservoir is surrounded with an impermeable wall forming material. The material can be applied by molding, spraying or clipping the pressed, shaped blend with the wall forming material. In another embodiment, the wall can be cast into a film, shaped to the desired dimensions to define a compartment that is filled with beneficial agent and then closed. The device can also be manufactured with an empty compartment that is filled through the orifice. The system when formed of more than one wall forming material can be joined by various joining techniques such as high frequency electronic sealing that provides clean edges and firmly sealed devices. The device can also be made by coextruding the wall and the reservoir through a die having two predimensional apertures. Another, and presently preferred, technique that can be used to apply the wall forming material to a compartment is the air suspension procedure. This procedure consists in suspending and tumbling the pressed agents in a current of air until the wall is applied to said agents. The air suspension procedure is described in U.S. Pat. No. 2,799,241; in *J. Am. Pharm. Assoc.*, Volume 8, pages 451 to 459, 1959; and ibid, Volume 49, pages 82 to 84, 1960. Other standard manufacturing procedures are described in *Modern Plastics Encyclopedia*, Volume 46, pages 62 to 70, 1979; and in *Pharmaceutical Sciences*, by Remington, Fourteenth Edition, pages 1626 to 1678, 1970, published by Mack Publishing Company, Easton, Pa.

Exemplary solvents suitable for manufacturing the wall include inert, inorganic and organic solvents that do not adversely harm the materials, agents and the final device. The solvents broadly include members selected from the group consisting of aqueous solvents, alcohols, ketones, esters, ethers, aliphatic hydrocarbons, halogenated solvents, cycloaliphatics, aromatics, heterocyclics, and mixtures thereof. Typical solvents include acetone, diacetone, alcohols, methanol, ethanol, isopropyl, butyl alcohols, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloridde and methanol, ethylene dichloride and methanol, and the like.

The following examples are merely illustrative of the present invention, and they should not be considered a limiting the scope of the invention in any way, as these examples and other equivalents thereof will become more apparent to those versed in the art in the light of the present disclosure, the drawings and the accompanying claims.

EXAMPLE 1

In the present example, the results provided by the devices of this invention are distinguished with the results provided by the prior art as represented by U.S. Pat. Nos. 3,851,648 and 3,924,622.

Generally, the amount of drug released per unit time by a device of the prior art is governed by Fick's Law:

$$dm/dt = A/l \cdot D \cdot C_s \quad (1)$$

wherein $dm/dt$ is the mass of agent released per unit time, A is the area of the releasing surface, 1 is the path length drug must travel from surface, separating the dispersed drug from the dissolved drug, to the outside of the device, and D is the diffusion coefficient of the drug in the fluid that enters the device, and $C_s$ is the solubility of drug in the relaxed medium in the device.

The amount of drug released from a device for the claimed invention is governed by equation (2).

$$dm/dt = C_m \cdot A \cdot ds/dt \quad (2)$$

for very soluble drugs with the members of the equation as defined below, wherein $dm/dt$ is the mass of agent released per unit time, A is the area of the releasing surface and it is a constant for the claimed device, $ds/dt$ is the speed of travel of the relaxing front, and $C_m$ is the drug concentration in the unrelaxed matrix.

For very soluble drugs, it can be assumed the rate of diffusion from the device through the relaxed polymer is large compared to the rate at which drug is liberated by relaxation, as is demonstrated in Example 2. Through selection of this mechanism, a device can be designed free of selecting shapes which increase in surface area to keep the delivery rate constant as in the prior art, rather the release rate is maintained constant by the constant speed of relaxation.

For drugs of limited solubility, which diffuse in aqueous media at low rates, the release rate from the system is expressed by equation (3), which closely resembles equation (2), when highly swellable polymers are used in the device. Equation is as follows:

$$dm/dt = A \cdot ds/dt \cdot C_m - ds/dt \cdot A \cdot C_r \qquad (3)$$

The symbols in equation (3) have the same meaning as in equation (2), and in addition, $C_r$ is the drug concentration in the relaxed part of the matrix, which in first approximation is given by equation (4).

$$C_r = C_m \cdot V_d / V_w \qquad (4)$$

wherein Vd is the polymer volume in the dry state, and Vw the volume of the same mass of polymer in the wet state, that is the relaxed state.

The relaxed rate (3) in this case is again a constant for polymers with constant speeds of relaxation (ds/dt), and constant surface A. The total amount of drug m released at any given time t from the system s is then obtained by integrating equation (3), which results in equation (5).

$$m = A \cdot s (C_m - C_r) \qquad (5)$$

wherein s is the total distance the front has traveled. It is assumed that all the drug which has been extruded from the system is dispersed into the surrounding medium. The fraction of drug not delivered at constant rate is mnz/mt, and in equation (6).

$$mnz/mt = C_r/C_m = V_d/V_w \qquad (6)$$

where, $C_r$ can be minimized by selecting polymers which swell to a significant degree such that $V_w = V_d$.

EXAMPLE 2

A device for dispensing a benefical agent to a biological environment of use is manfuactured as follows: first, a 21 mm length of poly(vinyl chloride) wall forming polymer having an outside diameter of 7.2 mm that surrounds and defines an internal compartment having an inside diameter of 4.5 mm, with two orifices in spaced relation positioned at the ends of the device, is filled with a reservoir forming formulation. The formulation consists essentially of 95% water swellable starch for the formula $(C_6H_{10}O_5)_x$ wherein x is $1 \times 10^3$ to $6 \times 10^6$, having mixed therein 5% procainamide hydrochloride, the beneficial agent. Then the formulation is compacted into a unit reservoir in the compartment by applying pressure against the formulation at each orifice.

Next, score lines are scribed at 1 mm intervals along the length of the device and the device placed in a beaker containing 100 ml of distilled water at 37° C. The amount of procainamide hydrochloride relased per unit time over prolonged time is measured with a UV-spectrometer. The progression of water absorption by the polymeric starch in the reservoir is visually observed during the releasing period. The rate of water imbition is measured for seven hours by measuring the distance the absorbed water penetrated from both orifices. The sum of the absorption distances from both orifices towards the center, is recorded as a function of time and compared to the amount of released procainamide hydrochloride. The results are shown in FIG. 7.

Figure 7:
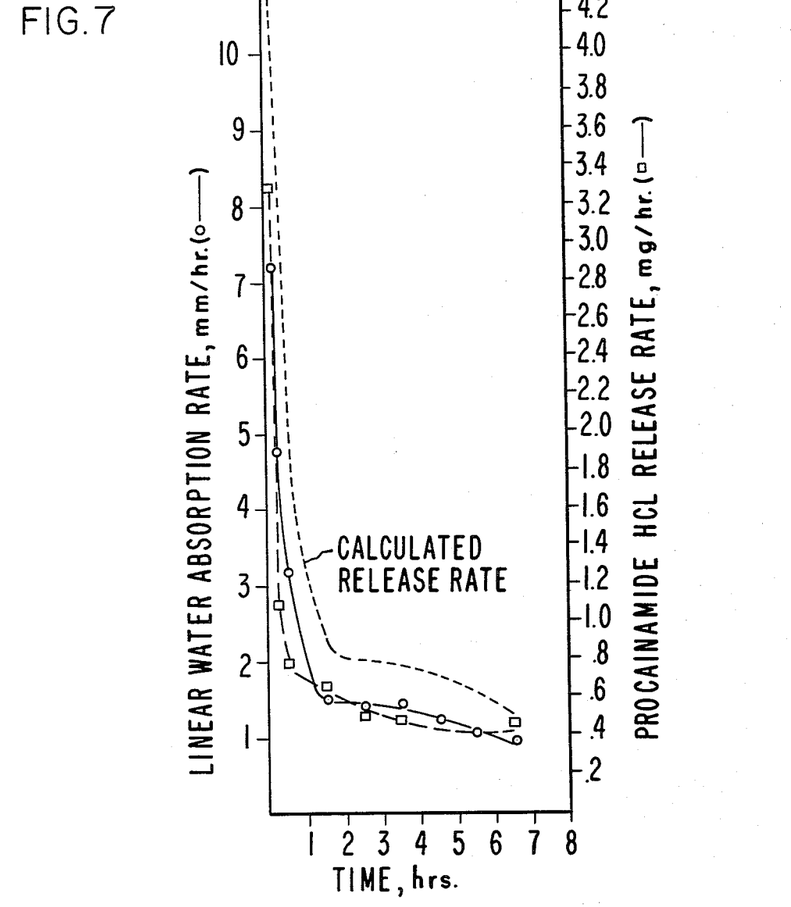

The results presented in FIG. 7 indicate the water soluble drug procainamide hydrochloride can be delivered at a controlled rate using the device of this invention, that the rate of release of procainamide hydrochloride is proportional to the imbibition velocity of water into the reservior of the device and that the rate of imbibition and the rate of procainamide hydrochloride delivered are substantially zero order over time.

The measured rate of release for procainamide hydrochloride is compared with the calculated rate of release determined by the following equations:

$$dm/dt = ds/dt \cdot A \cdot C = dv/dt \cdot C$$

wherein s is distance the imbibed water must travel in the device, A is the cross-sectional area inside the device, and C is the concentration of the procainamide hydrochloride in the device, which for this example is as follows:

$$dm/dt = ds/dt(0.15 \text{ cm}^2)(40 \text{ mg/cm}^3) = ds/dt(6.0 \text{ mg/cm})$$

The calculated rate of release is compared with the actual rate of release, in FIG. 7.

EXAMPLE 3

A dispensing device for the controlled and continuous release of progesterone is manufactured as follows: first, 5 grams of progesterone, 10 grams of poly(vinyl pyrrolidone), 20 grams of mannitol and 65 grams of cross-linked dextran are thoroughly mixed in a v-blender to produce a reservoir forming drug formulation. Then, the blend is transferred to a Manesty machine and the formulation compressed under $5 \times 10^3$ lb/sq. in. Next, the pressed formulations are surrounded with a laminate comprising an inner lamina of semipermeable cellulose acetate having an acetyl content of 32%. The lamina is formed by using a Wurster air suspension machine from a 5% polymer solution in acetone. Next, an outer lamina formed of fluid impermeable poly(vinyl chloride) in tetrahydrofuran is laminated to the inner lamina by dipping the device into the lamina-forming polymer. Then, the devices are air dried, and after drying, an orifice is drilled to yield the final device. The orifice functions for fluid intake and delivery of drug.

Figure 8:
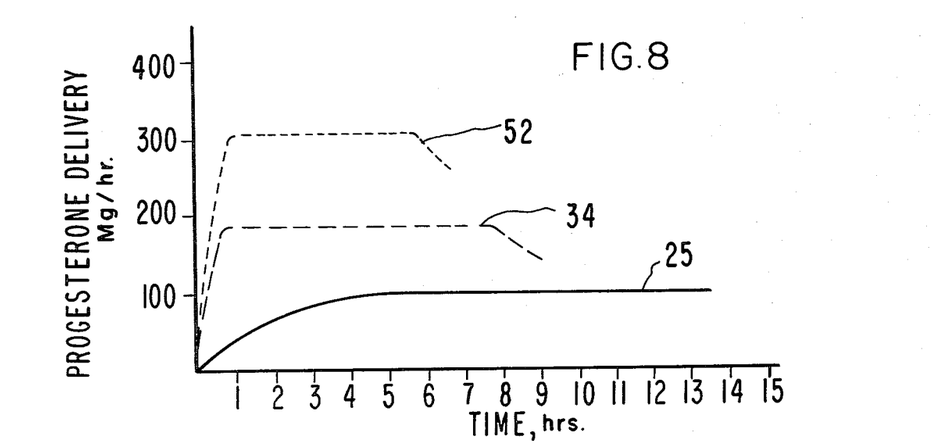
Figure 9:
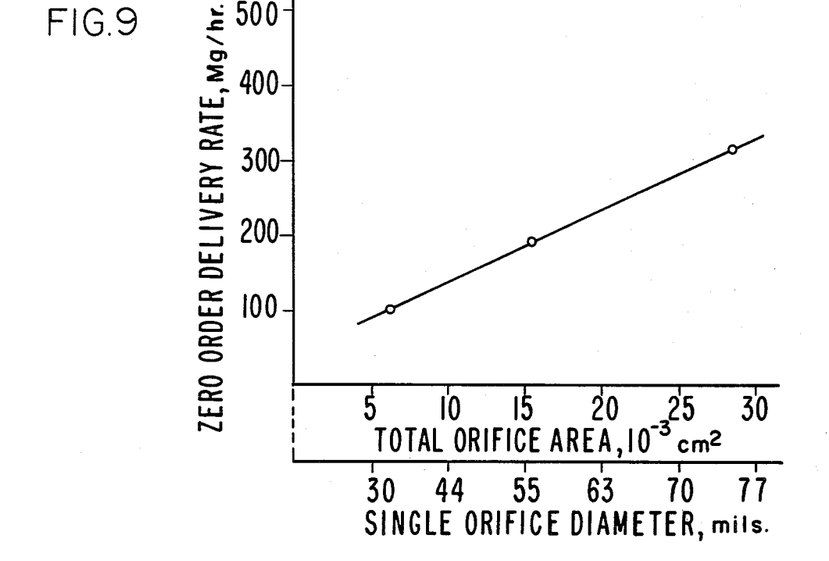

FIG. 8 shows the rate of delivery for the substantially wate insoluble drug progesterone as released by device made according to the instant example. In FIG. 8, the continuous line indicates a device whose orifices are 25 mil in diameter, the dashed line indicates a device whose orifices are 34 mil in diameter, and the dotted line a device whose orifices are 52 mil in diameter. Numbers 1–15 is time in hours. FIG. 9 illustrates the rate of release for the device by comparing the diameter for a single orifice against the total area of the orifice.

EXAMPLE 4

Figure 10:
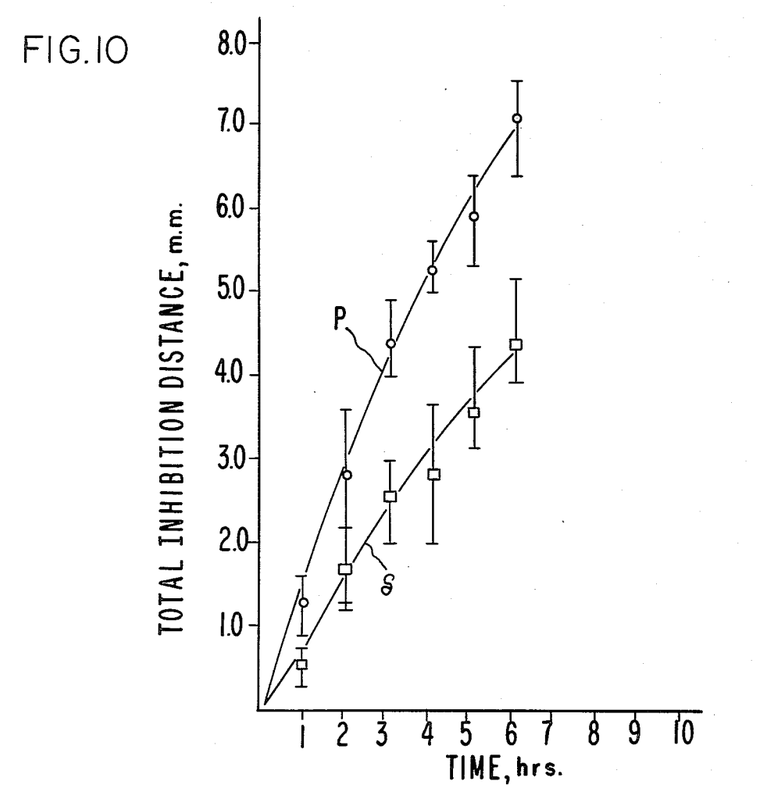

The procedure of Example 2 is repeated with the present example substituting for the dextran used above, a dextran selected from the group consisting essentially of diethylaminoethyl dextran, diethyl(2-hydroxypropyl) aminoethyl dextran, carboxymethyl dextran, and sulphopropyl dextran. The two dextrans having the diethylamninoethyl group are anionic, and the dextrans having the carboxymethyl and sulphopropyl group are cationic resins. In accompanying FIG. 10 the imbibition distance water moves in devices having dextran polymeric agents is depicted for the drugs procainamide hydrochloride and progesterone. In the Figure, the letter S indicates the water imbibition distance for 3 devices containing 5% progesterone, and the letter P indicates the average water imbibition distance for 5 devices housing 10% procainamide hydrochloride.

EXAMPLE 5

The procedures of Examples 1 to 3 are repeated for these devices having a reservoir housing poly(1,4-glucopyranose) containing progesterone or procainamide hydrochloride. The devices have a single orifice of 4 mm or 3.2 mm. The calculated rate of release for a device having an orifice of 4 mm and housing progesterone is 8.2 mg of progesterone for each cm of imbibition of water by the polymer in the device; for a device having an orifice of 3.2 mm and housing progesterone, 6.6 mg of progesterone is released for each cm of water imbibition; and, for a device having an orifice of 3.2 mm and housing procainamide hydrochloride with a rate of release of 11.0 mg for each cm of water imbibition.

EXAMPLE 6

A device for dispensing progesterone is made as follows: first, 5 wt% (weight percent) of progesterone, 10 wt% of poly(vinyl pyrrolidone), 20 wt% of mannitol, 65 wt% of cross-linked sulfonated copolymer of styrene and divinyl benzene, and a trace of non-toxic blue dye, are thoroughly blended into a homogeneous mass, and pressed under pressure into a shaped, compacted prereservoir. Next, the prereservoir is surrounded with a wall consisting essentially of an inner lamina of semipermeable cellulose acetate having an acetyl content of 39.8%, and an outer lamina of fluid and compound impermeable poly(vinylidene chloride). The outer lamina is applied from butanone and it is 3 mils thick. Then, two orifices having 29 mil diameters are drilled through the final wall connecting the exterior of the device with the reservoir. The device has a total area of 1.51 cm$^2$, a volume of 0.139 cm$^3$, a weight of 135 mg, and an average release rate of 0.6 mg per hour.

EXAMPLE 7

A device for dispensing the steroid progesterone is made as follows: first, a homogeneous blend is made by blending progesterone, 10% by weight, mannitol, 30% by weight, and poly(acrylamide), 60% by weight. The blend is fed into an extruder which coextrudes bicylindrical device, with the blend in the interior, and ethylene-vinyl propionate, having a vinyl propionate content of 60%, extruded as the surrounding fluid impermeable wall. The blend consists of 50% of the device weight. A pelletizer then produces devices, of desired length housing the specific amount of drug.

EXAMPLE 8

The procedure of Example 6 is followed in this example. In this example, a three-layered device is coextruded containing (a) an outer wall of ethylene-vinyl propionate, 60% vinyl propionate, 20 mils thick; (b) a middle reservoir containing the blend of Example 6, 20 mils thick; and (c) an inner wall of ethylene-vinyl propionate, 60% vinyl propionate, 20 mils thick. The devices are simultaneously cut after coextrusion, and heat sealed on a hot bar to predetermined shapes. The heat sealing joins the two walls, and the orifice size is controlled by the fraction of the device perimeter that is not heat sealed by the manufacture.

While the invention has been described and illustrated in detail, it is not intended to be limited to the details and embodiments disclosed, since various modifications and changes may be made without departing in any way from the spirit of the present invention.

We claim:

1. A dispenser for the controlled dispensing of a beneficial agent to a fluid environment of use, the dispenser comprising:
   (a) a container having a wall impermeable to fluid and impermeable to agent, said wall surrounding an internal reservoir having an uniform measurement along a given dimension;
   (b) a passageway in the container connecting the reservoir with the exterior of the dispenser, said passageway having an area that permits entry of fluid into the reservoir, and release of beneficial agent from the reservoir;
   (c) means in the reservoir for dispensing the beneficial agent from the dispenser, said means (1) occupying a volume having a constant cross-sectional area parallel to the passageway and housing the beneficial agent therein, (2) absorbs fluid that enters the reservoir and undergoes fluid induced relaxation from an unrelaxed to a relaxed state, with (3) the beneficial agent exhibiting an increased coefficient of diffusion in the relaxed means; and,
   (d) wherein, when the dispenser is in operation in the fluid environment of use, beneficial agent is dispensed by diffusion through the relaxed means and the passageway at a controlled rate from the dispenser in an amount that corresponds to the amount of agent within the means that goes from an unrelaxed to a relaxed state, which relaxation occurs at a rate governed by the progressive fluid absorption and accompanying induced relaxation of the means over time.

2. The dispenser for dispensing the beneficial agent according to claim 1, wherein the dispenser has two passageways.

3. The dispenser for dispensing the beneficial agent according to claim 1, wherein the means is lightly cross-linked.

4. The dispenser for controlled dispensing of a beneficial agent to the fluid environment according to claim 1, wherein the beneficial agent is a drug and the environment of use to an animal.

5. The dispenser for the controlled dispensing of a beneficial agent according to claim 1, wherein the dispenser is sized, shaped and adapted for dispensing beneficial agent to an oral environment of use, and said agent is a drug.

6. The dispenser for the controlled dispensing of a beneficial agent according to claim 1, wherein the dispenser is sized, shaped and adapted for dispensing a beneficial agent to an anal environment of use.

7. The dispenser for the controlled dispensing of a beneficial agent according to claim 1, wherein the dispenser is sized, shaped and adapted for dispensing beneficial agent to an ocular environment.

8. A dispenser for the controlled dispensing of a beneficial agent to a fluid environment of use, wherein said dispenser comprises:
   (a) a container impermeable to fluid and impermeable to agent;
   (b) a reservoir in the container;
   (c) a passageway in the container connecting the reservoir with the exterior of the dispenser, said passageway having an opening that permits the entry of fluid into the reservoir and release of agent from the reservoir;
   (d) means for housing and dispensing the beneficial agent from the dispenser in the reservoir, said means a transporting agent that occupies a volume having a constant cross-sectional area parallel to the passageway, absorbs fluid that enters the reservoir, undergoes relaxation, and flows through the passageway to the exterior of the dispenser transporting the agent therewith; and,
   (e) wherein, when the dispenser is in operation, the agent is dipensed in a controlled amount to the environment of use at a rate governed by the rate of relaxation and flow of the transporting means from the dispenser over a prolonged period of time.

9. The dispenser for the controlled dispensing of the beneficial agent according to claim 8, wherein the beneficial agent is a drug, and the environment of use is an animal.

10. The dispenser for the controlled dispensing of the beneficial agent according to claim 8, wherein the dispenser has two passageways.

11. The dispenser for the controlled dispensing of the beneficial agent according to claim 8, wherein the means is lightly cross-linked.

12. The dispenser for the controlled dispensing of the beneficial agent according to claim 8, wherein the dispenser is sized, shaped and adapted for dispensing a beneficial agent to an oral environment of use.

13. The dispenser for the controlled dispensing of the beneficial agent according to claim 8, wherein the dispenser is sized, shaped and adapted for dispensing the beneficial agent to an anal environment of use.

14. The dispenser for the controlled dispensing of the beneficial agent according to claim 8, wherein the dispenser is sized, shaped and adapted for dispensing the beneficial agent to an ocular environment of use.

15. The dispenser for the controlled dispensing of the beneficial agent according to claim 8, wherein the passageway has an area that permits the simultaneous entry of fluid into the reservoir and the release of beneficial agent from the reservoir, and the transporting agent maintains a constant cross-sectional area in reference to the passageway.

16. The dispenser for the controlled dispensing of the beneficial agent according to claim 8, wherein the fluid is water.

17. The dispenser for the controlled dispensing of the beneficial agent according to claim 8, wherein the beneficial agent is a member selected from the group consisting of central nervous system, autonomic nervous system, hypnotic, sedative, psychic energizers, tranquilizers, anticonvulsants, muscle relaxants, antiparkinson, analgesic, antipyretic, anti-inflammatory, anesthetic, antispasmodic, muscle contractant, antimicrobial, antimalarial, hormonal, progestational, estrogenic, androgenic, corticoid, sympathomimetic, cardiovascular, diuretic, antiparasite, neoplastic, hypoglycemic, nutritional, vitamin, and ocular drugs.

18. The dispenser for the controlled dispensing of the beneficial agent according to claim 8, wherein the dispenser has two passageways and the means has an uniform cross-sectional area parallel to the passageways during the dispensing period.

19. The dispenser for the controlled dispensing of the beneficial agent to a fluid environment of use, said dispenser comprising:
   (a) a container having a wall that surrounds an internal reservoir, said wall formed of a polymer selected from the group consisting of acrylonitrile-styrene copolymer, acrylonitrile-butadiene-styrene terpolymer, poly(monochlorotrifluoroethylene), poly(tetrafluorethylene), tetrafluoroethylenehexafluoroethylene copolymer, poly(vinylidene chloride), vinylidene chloride-vinyl chloride copolymer, poly(styrene), butadiene-styrene copolymer, chlorosulfonated polyethylene-styrene copolymer, vinyl chloride-acrylonitrile copolymer, poly(vinyl chloride), vinylidene chloride-alkylacrylate copolymer, poly(cyclohexane-dimethanolterphthalate), poly(carbonate) and rubber;
   (b) a passageway in the container connecting the reservoir with the exterior of the device, said passageway having an area that permits the entry of fluid into the reservoir, and the release of agent from the reservoir; and,
   (c) means in the reservoir for dispensing the agent from the dispenser, said means (1) containing the agent mixed therein, (2) absorbs fluid that enters the reservoir and undergoes fluid induced relaxation from an unrelaxed to and relaxed state, with (3) the agent exhibiting an increased coefficient of diffusion in the relaxed state, and (4) passing through the relaxed means and the passageway to the exterior of the dispenser for dispensing of agent at a controlled rate over time.

20. A dispenser for the controlled dispensing of a beneficial agent to a fluid environment of use, said dispenser comprising:
   (a) a container having a wall that surrounds and forms an internal reservoir, said wall a polymer selected from the group consisting of acrylonitrile-styrene copolymer, acrylonitrile-butadiene-styrene terpolymer, poly(monochlorotrifluoroethylene), poly(tetrafluoroethylene), tetrafluoroethylenehexafluoroethylene copolymer, poly(vinylidene halide), poly(vinylidene chloride), vinylidene chloride-vinyl chloride copolymer, polymer(styrene), butadiene-styrene copolymer, chlorosulfonated polyethylene-styrene copolymer, vinyl chloride-acrylonitrile copolymer, poly(vinyl chloride), vinylidene chloride-acrylonitrile copolymer, poly(vinyl chloride), vinylidene chloride-alkylacrylate copolymer, poly(cyclohexane dimethanol-terphthalate), poly(carbonate) and rubber;
   (b) a passageway in the container wall connecting the reservoir with the exterior of the dispenser, said passageway having an area that permits the entry of fluid into the reservoir and the release of agent from the reservoir, and, (c) means for dispensing the beneficial agent from the device in the reservoir, said means a transporting agent having the agent therein, which means absorbs fluid that enters the reservoir, undergoes relaxation and flows through the passageway to the exterior of the dispenser transporting the agent concurrently therewith at a controlled rate governed by the rate of relaxation of the transporting means over time.

21. A dispenser for the controlled dispensing of a beneficial agent to a biological fluid environment of use, wherein said dispenser comprises:
 (a) container having a wall impermeable to fluid and impermeable to agent, said wall surrounding an internal reservoir;
 (b) a passageway in the wall connecting the reservoir with the exterior of the dispenser, said passageway having an opening that permits the entry of the biological fluid into the reservoir and release of agent from the reservoir;
 (c) means in the reservoir housing the agent, said means absorbing fluid that enters the reservoir and undergoes fluid induced relaxation from an unrelaxed to a relaxed means with the agent exhibiting an increased coefficient of diffusion in the relaxed means, which means is a member selected from the group consisting of poly(hydroxyalkyl methacrylate), poly(acrylamide), poly(methacrylamide), poly(N-vinyl-2-pyrrolidone), dextrin, anionic and cationic hydrogels, organic poly(electrolyte) complexes, poly(alkylene oxide), lightly cross-linked poly(vinyl alcohol), poly(glyceryl methacrylate), poly(hydroxypropyl methacrylate), poly(sulphide), poly(sulphoxide), poly(sulphone), poly(styrene), copolymeric divinylbenzene-styrene, poly(diakylaminoethyl styrene), cation-exchange resins, anion-exchange resins, sulfonated copolymers of styrene and divinyl-benzene, copolymers of methacrylic acid and divinylbenzene; and,
 (d) wherein, when the dispenser is in operation in the fluid environment of use, beneficial agent is dispensed by diffusion through the relaxed means and the passageway from the dispenser at a rate governed by the progressive fluid absorption and accompanying fluid induced relaxation of the means over a prolonged period of time.

22. A dispenser for dispensing a beneficial agent at an oscillating rate of release to a fluid environment of use, wherein said dispenser comprises:
 (a) a container having a wall made of a material that is substantially impermeable to the passage of fluid and substantially impermeable to the passage of agent, which wall surrounds and forms;
 (b) an internal reservoir having a cross-sectional area that changes periodically from a maximum to a minimum area along one dimension;
 (c) a passageway in the wall of the container connecting the reservoir with the exterior of the dispenser;
 (d) means in the reservoir for dispensing the beneficial agent from the dispenser, said means having a cross-sectional area that corresponds to the reservoir, houses the beneficial agent, and absorb fluid and undergoes relaxation; and,
 (e) wherein, when the dispenser is in operation, fluid enters the reservoir, with the beneficial agent dispensed at an oscillating rate in an amount that corresponds to the amount of agent in the means that undergoes relaxation as it cross-sectional area changes throughout the device.

23. The dispenser for dispensing the beneficial agent according to claim 22, wherein the wall exhibits a frequency of change in shape that corresponds to the periodic changes of the reservoir.

24. A dispenser for dispensing a beneficial agent at an oscillating rate of release to a fluid environment of use, wherein said dispenser comprises:
 (a) a container having a wall made of a material that is substantially impermeable to the passage of fluid and substantially impermeable to the passage of agent, which wall increases in length outwardly then decreases in length inwardly along the axis of the device over the length of the device, which wall surrounds and forms:
 (b) an internal reservoir having a cross-sectional area that changes periodically from a maximum to a minimum area along one dimension;
 (c) a passageway in the wall of the container connecting the reservoir with the exterior of the dispenser;
 (d) means in the reservoir for dispensing the beneficial agent from the dispenser, said means having a cross-sectional area that corresponds to the reservoir, houses the beneficial agent, and absorbs fluid and undergoes relaxation; and,
 (e) wherein, when the dispenser is in operation fluid enters the reservoir, with the beneficial agent dispensed at an oscillating rate in an amount that corresponds to the amount of agent in the means that undergoes relaxation as it cross-sectional area changes throughout the device.

25. A dispenser for dispensing a beneficial agent in a fluid environment of use at a gradually increasing rate of release followed by a substantially zero order rate of release over a prolonged period of time, wherein said device comprises:
 (a) a container having a wall made of a material that is substantially impermeable to the passage of fluid and substantially impermeable to the passage of agent, said container having a lead end that gradually increases in size followed by the remainder of the container having constant dimensions, with the wall surrounding and forming;
 (b) an internal reservoir;
 (c) a passageway in the lead end of the wall connecting the reservoir with the exterior of the device;
 (d) means in the reservoir for dispensing agent from the dispenser, said means occupying a shape that corresponds to the shape of the reservoir, housed the beneficial agent, absorbs fluid and undergoes relaxation in the presence of the fluid, and,
 (e) wherein, when the dispenser is in the environment of use, fluid enters the reservoir urging the means to undergoes relaxation, which dispenses agent from the device at a gradually increasing rate followed by a zero order rate that corresponds to shape and rate at which the means undergoes relaxation over time.

* * * * *